(12) United States Patent
Doi et al.

(10) Patent No.: US 10,702,691 B2
(45) Date of Patent: Jul. 7, 2020

(54) LOW-FREQUENCY TREATMENT DEVICE, MAIN BODY PORTION FOR LOW-FREQUENCY TREATMENT DEVICE, PAD FOR LOW-FREQUENCY TREATMENT DEVICE, COMBINATION OF PAD AND HOLDER FOR LOW-FREQUENCY TREATMENT DEVICE

(71) Applicant: OMRON HEALTHCARE CO., LTD., Muko-shi, Kyoto (JP)

(72) Inventors: Yoshiki Doi, Kyoto (JP); Shinji Nakazawa, Kyoto (JP); Kayoko Maeda, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 180 days.

(21) Appl. No.: 15/902,293

(22) Filed: Feb. 22, 2018

(65) Prior Publication Data

US 2018/0177998 A1 Jun. 28, 2018

Related U.S. Application Data

(63) Continuation of application No. PCT/JP2016/073997, filed on Aug. 17, 2016.

(30) Foreign Application Priority Data

Sep. 4, 2015 (JP) .................................. 2015-174547
Jul. 7, 2016 (JP) .................................. 2016-135124

(51) Int. Cl.
*A61N 1/04* (2006.01)
*A61N 1/32* (2006.01)

(52) U.S. Cl.
CPC ............. *A61N 1/0492* (2013.01); *A61N 1/04* (2013.01); *A61N 1/0452* (2013.01); *A61N 1/32* (2013.01); *A61N 1/048* (2013.01); *A61N 1/321* (2013.01)

(58) Field of Classification Search
CPC .... A61N 1/0452–0492; A61N 1/36014–36028
See application file for complete search history.

(56) References Cited

U.S. PATENT DOCUMENTS 4,033,356 A * 7/1977 Hara .................... A61N 1/0452
607/152
6,445,955 B1 * 9/2002 Michelson ......... A61N 1/36003
607/2

(Continued)

FOREIGN PATENT DOCUMENTS

JP    S52-141283 U    10/1977
JP    S57-185188 U    11/1982

(Continued)

OTHER PUBLICATIONS

Nov. 22, 2016 International Search Report issued in International Patent Application No. PCT/JP2016/073997.

*Primary Examiner* — Eric D. Bertram
(74) *Attorney, Agent, or Firm* — Oliff PLC

(57) ABSTRACT

A low-frequency treatment device includes: a pad configured to be attached to a body of a user; a holder configured to hold the pad; and a main body portion configured to be attached to the holder. The holder and the main body portion are engaged, with a clearance of a predetermined distance for arranging the pad being formed therebetween. Electrical conduction established between a pad-side electrode portion included on the pad and a main body portion-side electrode portion included on the main body portion by coming into contact with each other in the clearance of the predetermined distance. At least one electrode portion among the pad-side (Continued)

electrode portion and the main body portion-side electrode portion can perform movement in a direction of approaching and separating from the other electrode portion and is biased in the approaching direction.

6 Claims, 10 Drawing Sheets

(56) References Cited

U.S. PATENT DOCUMENTS

| | | | | |
|---|---|---|---|---|
| 6,961,622 | B2* | 11/2005 | Gilbert | A61H 39/002 607/148 |
| 2015/0231393 | A1 | 8/2015 | Bachinski et al. | |
| 2017/0209693 | A1* | 7/2017 | An | A61N 1/0476 |
| 2018/0177998 | A1* | 6/2018 | Doi | A61N 1/04 |

FOREIGN PATENT DOCUMENTS

| | | |
|---|---|---|
| JP | H03-096855 U | 10/1991 |
| JP | H05-003924 A | 1/1993 |
| JP | H06-339531 A | 12/1994 |
| JP | H08-243175 A | 9/1996 |
| JP | 2601102 Y2 | 11/1999 |

* cited by examiner

LOW-FREQUENCY TREATMENT DEVICE, MAIN BODY PORTION FOR LOW-FREQUENCY TREATMENT DEVICE, PAD FOR LOW-FREQUENCY TREATMENT DEVICE, COMBINATION OF PAD AND HOLDER FOR LOW-FREQUENCY TREATMENT DEVICE

TECHNICAL FIELD

The present invention relates to a low-frequency treatment device.

BACKGROUND ART

Conventionally, there has been a low-frequency device that performs a treatment such as relieving shoulder stiffness of a user due to a pad that includes a conductive layer being attached to the body of the user and a low-frequency pulse current being supplied to the body (see Patent Document 1).

With the low-frequency treatment device disclosed in Patent Document 1, a main body portion ("upper-half portion" in Patent Document 1) is attached to a holder ("lower-half portion" in Patent Document 1) with a pad ("electrode pad" in Patent Document 1) interposed therebetween. Application of current to the pad is performed due to a terminal provided on the holder being electrically connected to the main body portion and the pad.

The electrical connection between the holder and the main body portion is established due to an electrode portion ("connection terminal" in Patent Document 1) provided on the main body portion coming into contact with an electrode portion ("connection terminal" in Patent Document 1) provided so as to protrude from the holder.

However, with this configuration, the electrical connection is established due to the holder-side electrode portion and the main body portion-side electrode portion merely coming into contact with each other. Also, the contact is held due to the fitting together of a recess and a protrusion of the holder and the main body portion. For this reason, for example, if slack is generated in the fitting together of the recess and the protrusion, connection failure occurs, as a result of which the application of current to the pad becomes unstable in some cases.

In this manner, the low-frequency treatment device according to Patent Document 1 has had room for improvement in that application of current to the pad becomes unstable in some cases.

CITATION LIST

Patent Literature

Patent Document 1: JP H6-339531A (FIGS. 3 and 4)

SUMMARY OF INVENTION

Technical Problem

In view of this, the present invention aims to provide a low-frequency treatment device, a main body portion for a low-frequency treatment device, a pad for a low-frequency treatment device, and a combination of a pad and a holder for a low-frequency treatment device, according to which it is possible to stably apply current to a pad.

Solution to the Problem

The present invention is a low-frequency treatment device includes: a pad configured to be attached to a body of a user and to supply a low-frequency pulse current to the user, the pad including a pad-side electrode portion; a holder configured to hold the pad; and a main body portion configured to be attached to the holder, the main body portion including a main body portion-side electrode portion configured to be connected to the pad-side electrode portion for electrical conduction and to supply a low-frequency pulse current thereto. The holder and the main body portion are engaged with a clearance of a predetermined distance for arranging the pad being formed therebetween, the electrical conduction is established between the pad-side electrode portion and the main body portion-side electrode portion due to coming into contact with each other in the clearance of the predetermined distance, at least one electrode portion among the pad-side electrode portion and the main body portion-side electrode portion can perform movement in a direction of approaching and separating from the other electrode portion and is biased in an approaching direction, and the electrical conduction is established in the one electrode portion in a range in which the movement is possible.

With this configuration, at least one electrode portion among the pad-side electrode portion and the main body portion-side electrode portion is connected to the other electrode portion for electrical conduction while being biased in the approaching direction in the range in which the movement in the direction of approaching and separating is possible. For this reason, even if slack is generated in the engagement between the holder and the main body portion, the biased electrode portion can follow the slack. In other words, since the electrical conduction is supported by the biasing, conduction failure can be suppressed.

Also, the main body portion-side electrode portion can include: an electrode body that can protrude and recede with respect to a case included in the main body portion, at least a portion of the electrode body being composed of a conductor, and an electrode biasing portion that biases the electrode body in a direction of protruding from the case.

With this configuration, the electrode body can be directly biased toward the pad-side electrode portion by the electrode biasing portion. Accordingly, the main body portion-side electrode portion can be given a simple configuration. Note that in this configuration, the electrode body and the electrode biasing portion can be formed integrally with each other.

Also, the electrical conduction in the main body portion-side electrode portion can be established due to its leading end portion coming into contact with the pad-side electrode portion, and the pad-side electrode portion can be composed of a planar conductor.

With this configuration, the electrical conduction is established due to the planar pad-side electrode portion coming into contact with the leading end portion of the biased main body portion-side electrode portion. For this reason, stable electrical conduction is possible.

Also, the pad-side electrode portion can have a greater thickness than another portion of the pad.

With this configuration, the pad-side electrode portion has a greater thickness than the other portion of the pad, and thus the biasing force of the electrode biasing portion is applied sufficiently. For this reason, the main body portion-side electrode portion is not likely to separate from the pad-side electrode portion.

Also, the main body portion can be removed from the holder by being rotated in plan view with respect to the holder, the holder can include a rotation restricting portion that restricts rotation of the main body portion in the attached state, and if the main body portion is at a position at which rotation is restricted by the rotation restricting portion, the electrical conduction can be established, and if the main body portion is not at a position at which rotation is restricted, the electrical conduction cannot be established due to the pad-side electrode portion and the main body portion-side electrode portion being separated from each other.

With this configuration, the electrical conduction is established only when the holder and the main body portion are in the attached state. For this reason, if attachment has not been performed correctly, current is not applied to the pad, which is safe.

Also, the holder can be composed of a non-conductor.

With this configuration, if the pad is arranged so as to span over the spine on the back of the user, the holder, which is a non-conductor, can be arranged aligned with the spine. Accordingly, it is possible to suppress a case in which a low-frequency pulse current flows in the spine and the spinal cord of the user. Accordingly, since it is possible to suppress a case in which the spine and the spinal cord are injured by the current, the low-frequency treatment device can be used safely.

Also, the holder can include: a pad holding portion configured to hold the pad on its upper surface; a pressing portion that is arranged on a side opposite to a side on which the main body portion-side electrode portion is arranged with respect to the pad-side electrode portion, the pressing portion being able to protrude and recede with respect to the pad holding portion; and a biasing portion that biases the pressing portion in a direction of protruding from the pad holding portion.

With this configuration, the pad-side electrode portion can perform movement in the direction of approaching and separating from the main body portion-side electrode portion and is biased in the approaching direction, and therefore even if slack is generated in the engagement between the holder and the main body portion, the biased pad-side electrode portion can follow the slack. In other words, since the electrical conduction is supported by the biasing, conduction failure can be suppressed. Note that in this configuration, the main body portion-side electrode portion need not be able to perform movement in the direction of approaching and separating from the pad-side electrode portion and need not be biased in the approaching direction. With this configuration as well, the pad-side electrode portion can perform movement in the direction of approaching and separating from the main body portion-side electrode portion and is biased in the approaching direction, and thus the electrical conduction is supported by the biasing of the pad-side electrode portion. For this reason, conduction failure is suppressed. Alternatively, in the above-described configuration, the main body portion-side electrode portion may perform movement in the direction of approaching and separating from the pad-side electrode portion and may be biased in the approaching direction. Since the electrical conduction is supported by the biasing of the main body portion-side electrode portion and the biasing of the pad-side electrode portion, conduction failure can be further suppressed.

Also, the present invention is a main body portion for a low-frequency treatment device including: a pad configured to be attached to a body of a user and to supply a low-frequency pulse current to the user, the pad including a pad-side electrode portion; and a holder configured to hold the pad, the main body portion being configured to be attached to a holder and including a main body portion-side electrode portion configured to be connected to a pad-side electrode portion for electrical conduction and to supply a low-frequency pulse current thereto. The main body portion engages with the holder, with a clearance of a predetermined distance for arranging the pad being formed between the main body portion and the holder, the electrical conduction is established due to the main body portion-side electrode portion coming into contact with the pad-side electrode portion in the clearance of the predetermined distance, and the main body portion-side electrode portion can perform movement in a direction of approaching and separating from the pad-side electrode portion and is biased in an approaching direction, and the electrical conduction is established in a range in which the movement is possible.

With this configuration, at least one electrode portion among the pad-side electrode portion and the main body portion-side electrode portion is connected to the other electrode portion for electrical conduction while being biased in the approaching direction in the range in which the movement in the direction of approaching and separating is possible. For this reason, even if slack is generated in the engagement between the holder and the main body portion, the biased electrode portion can follow the slack. In other words, since the electrical conduction is supported by the biasing, conduction failure can be suppressed.

Also, the present invention is a pad for a low-frequency treatment device configured to be attached to a body of a user and to supply a low-frequency pulse current to the user, the pad including a pad-side electrode portion. The pad is held by a holder, a main body portion is attached to the holder, the main body portion includes a main body portion-side electrode portion configured to be connected to the pad-side electrode portion for electrical conduction and to supply a low-frequency pulse current thereto, the holder and the main body portion are engaged with a clearance of a predetermined distance for arranging the pad being formed therebetween, the electrical conduction is established between the pad-side electrode portion and the main body portion-side electrode portion due to coming into contact with each other in the clearance of the predetermined distance, at least one electrode portion among the pad-side electrode portion and the main body portion-side electrode portion can perform movement in a direction of approaching and separating from the other electrode portion and is biased in an approaching direction, the electrical conduction in the one electrode portion is established in a range in which the movement is possible, the electrical conduction in the main body portion-side electrode portion is established due to its leading end portion coming into contact with the pad-side electrode portion, and the pad-side electrode portion is composed of a planar conductor.

With this configuration, the electrical conduction is established due to the planar pad-side electrode portion coming into contact with the leading end portion of the biased main body portion-side electrode portion. For this reason, stable electrical conduction is possible.

Also, the present invention is a combination of a pad and a holder for a low-frequency treatment device including: a pad configured to be attached to a body of a user and to supply a low-frequency pulse current to the user, the pad including a pad-side electrode portion; and a holder for holding the pad. The holder is attached to a main body portion, and the main body portion includes a main body portion-side electrode portion configured to be connected to the pad-side electrode portion for electrical conduction and to supply a low-frequency pulse current thereto, the holder and the main body portion are engaged with a clearance of a predetermined distance for arranging the pad being formed therebetween, the electrical conduction is established between the pad-side electrode portion and the main body portion-side electrode portion due to coming into contact with each other in the clearance of the predetermined distance, at least one electrode portion among the pad-side electrode portion and the main body portion-side electrode portion can perform movement in a direction of approaching and separating from the other electrode portion and is biased in an approaching direction, the electrical conduction in the one electrode portion is established in a range in which the movement is possible, the main body portion can be removed from the holder by being rotated in plan view with respect to the holder, the holder includes a rotation restricting portion that restricts rotation of the main body portion in the attached state, and the pad-side electrode portion is formed such that if the main body portion is at a position at which rotation is restricted by the rotation restricting portion, the electrical conduction is established, and if the main body portion is not at a position at which rotation is restricted, the electrical conduction is not established due to the pad-side electrode portion and the main body portion-side electrode portion being separated from each other.

With this configuration, the electrical conduction is established only when the holder and the main body portion are in the attached state. For this reason, if attachment has not been performed correctly, current is not applied to the pad, which is safe.

Also, the holder can be composed of a non-conductor.

With this configuration, if the pad is arranged so as to span over the spine on the back of the user, the holder, which is a non-conductor, can be arranged aligned with the spine. Accordingly, it is possible to suppress a case in which a low-frequency pulse current flows in the spine and the spinal cord of the user. Accordingly, since it is possible to suppress a case in which the spine and the spinal cord are injured by the current, the low-frequency treatment device can be used safely.

Also, the holder can include: a pad holding portion configured to hold the pad on its upper surface; a pressing portion that is arranged on a side opposite to a side on which the main body portion-side electrode portion is arranged with respect to the pad-side electrode portion, the pressing portion being able to protrude and recede with respect to the pad holding portion; and a biasing portion that biases the pressing portion in direction of protruding from the pad holding portion.

With this configuration, the pad-side electrode portion can perform movement in the direction of approaching and separating from the main body portion-side electrode portion and is biased in the approaching direction, and therefore even if slack is generated in the engagement between the holder and the main body portion, the biased pad-side electrode portion can follow the slack. In other words, since the electrical conduction is supported by the biasing, conduction failure can be suppressed. Note that in this configuration, the main body portion-side electrode portion need not be able to perform movement in the direction of approaching and separating from the pad-side electrode portion and need not be biased in the approaching direction. With this configuration as well, the pad-side electrode portion can perform movement in the direction of approaching and separating from the main body portion-side electrode portion and is biased in the approaching direction, and thus electrical conduction is supported by the biasing of the pad-side electrode portion. For this reason, conduction failure can be suppressed. Alternatively, in the above-described configuration, the main body portion-side electrode portion may perform movement in the direction of approaching and separating from the pad-side electrode portion and may be biased in the approaching direction. Since the electrical conduction is supported by the biasing of the main body portion-side electrode portion and the biasing of the pad-side electrode portion, conduction failure can be further suppressed.

Advantageous Effects of the Invention

With the present invention, even if slack is generated in the engagement between the holder and the main body portion, the biased electrode portion can follow the slack, and therefore conduction failure can be suppressed. Accordingly, application of current from the main body portion to the pad can be performed stably.

DESCRIPTION OF EMBODIMENTS

Figure 1:
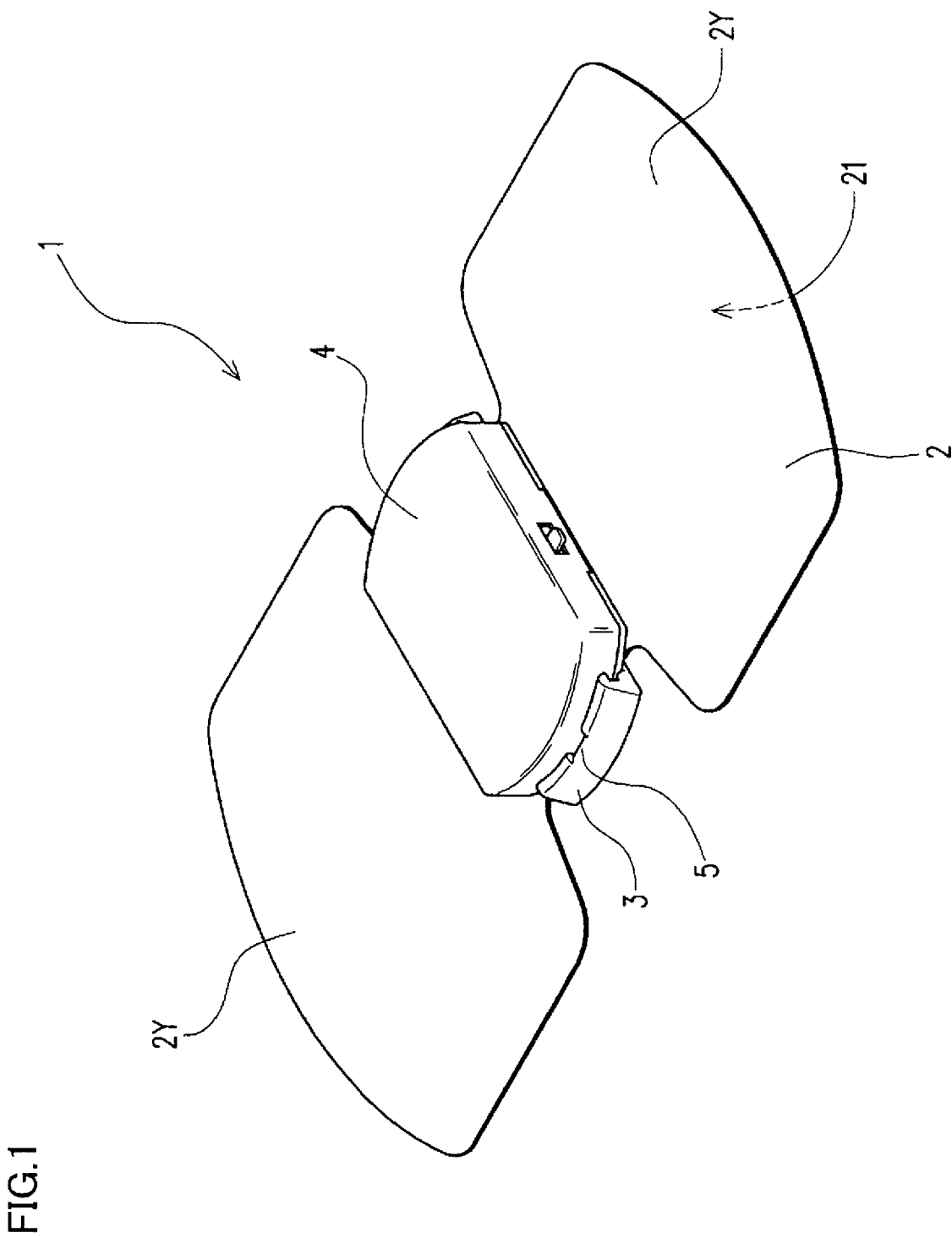
FIG. 1 is a perspective view showing a low-frequency treatment device according to an embodiment of the present invention.

Next, the present invention will be described by means of an embodiment. Note that the vertical direction in the following description is the vertical direction of a low-frequency treatment device 1 in the state shown in FIG. 1. The low-frequency treatment device 1 of the present embodiment is of a cordless type, includes a pad 2, a holder 3, and a main body portion 4 that are integrated at the time of use, and the low-frequency treatment device 1 can perform treatment with those units combined.

The pad 2 is a portion that is attached to the body of a user. The pad 2 includes conductive layers 2*a* that supply a low-frequency pulse current to the user. The conductive layers 2*a* are exposed on the surface (lower surface) of a body-side portion 21 facing the body side of the pad 2. The pad 2 is attached to the body of the user by adhering the body-side portion 21 to the skin of the user via conductive gel G (see FIG. 6).

The pad 2 is obtained by stacking carbon layers, which are conductive, through printing on the surface of a base material (not shown) made of a soft synthetic resin, and the carbon layers are the conductive layers 2*a*. The conductive layers 2*a* are provided according to their polarities (positive pole, negative pole) when current is applied. Note that since current is sometimes applied to the pad 2 with the polarities switched alternatingly, the polarities are variable instead of a positive pole-dedicated conductive layer 2*a* and a negative pole-dedicated conductive layer 2*a* existing in a fixed manner.

Figure 2:
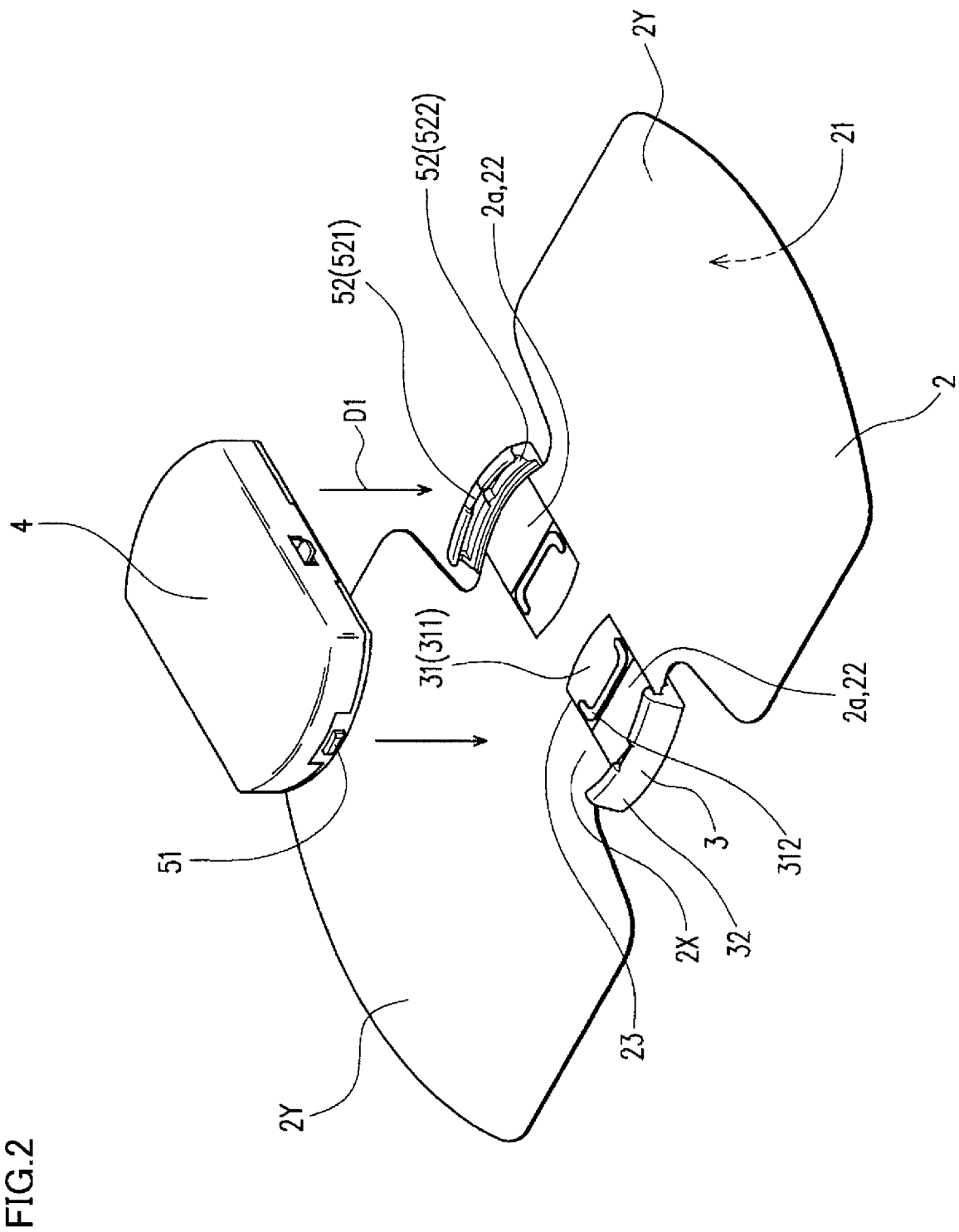
FIG. 2 is an exploded perspective view showing a state in which a holder and a pad of the low-frequency treatment device are separated from a main body portion.
Figure 3:
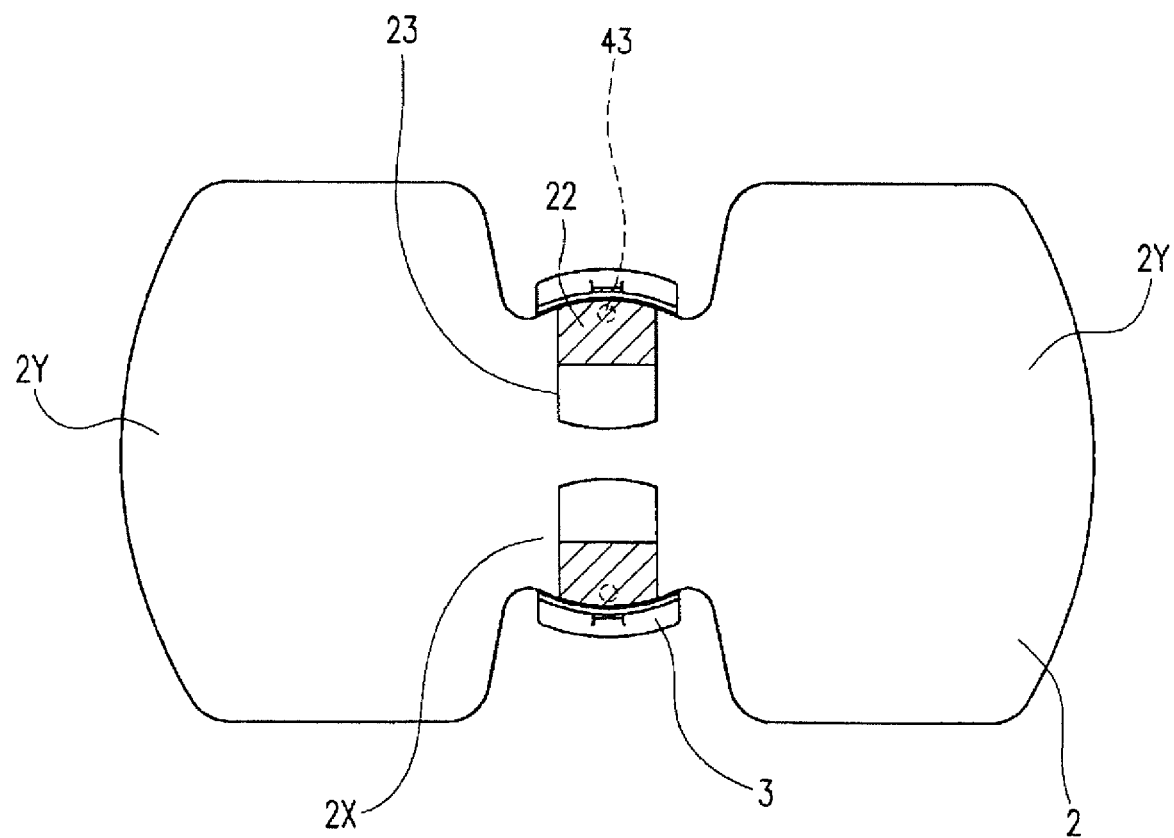
FIG. 3 is a plan view showing the holder and the pad of the low-frequency treatment device.

As shown in FIGS. 2 and 3, the pad 2 includes an attachment portion 2X that is attached to the holder 3, and treatment portions 2Y that extend in at least one direction from the attachment portion 2X and at which the conductive layers 2*a* are exposed. The treatment portions 2Y of the present embodiment extend in both directions from the attachment portion 2X according to their polarities. Also, the conductive layers 2*a* are exposed over the entire surface of the body-side portion 21, which is the bottom surface of the treatment portions 2Y.

The attachment portion 2X has a squeezed shape compared to the treatment portions 2Y. In other words, the width dimension of the attachment portion 2X is formed so as to be smaller than the width dimension of the treatment portions 2Y.

Accordingly, the holder 3 and the main body portion 4 can be made smaller. Also, the conductive layers 2*a* are exposed on the surface that faces the main body portion of the attachment portion 2X of the pad 2, and the exposed portions are pad-side electrode portions 22. In other words, the pad-side electrode portions 22 are composed of planar conductors (in the present embodiment, a carbon layer). The pad-side electrode portions 22 are formed for electrical connection with main body portion-side electrode portions 43. In the present embodiment, a conductive layer 2*a* corresponding to one pole (e.g., the positive pole) is exposed at one end in the width direction of the attachment portion 2X, and the conductive layer 2*a* corresponding to the other pole (e.g., the negative pole) is exposed at the other end. Accordingly, the conductive layers 2*a* of the pad-side electrode portions 22 are exposed at the outer circumferential portions of the pad 2. For example, the conductive layers 2*a* of the pad-side electrode portions 22 can be exposed by peeling off a layer of a portion of the pad 2, by folding over the pad 2 in the top-underside direction, or by overlaying the pad 2 on itself in the thickness direction. In particular, the pad-side electrode portions 22 can be made thicker than the other portions of the pad 2 by folding over the pad 2 in the top-underside direction or by overlaying the pad 2 on itself in the thickness direction. In this manner, if the pad-side electrode portions 22 are made thicker than the other portions of the pad 2, the main body portion-side electrode portion 43 is biased in the thickness direction of the pad 2, and therefore the greater the thickness is, the less likely the main body portion-side electrode portions 43 are to separate from the pad-side electrode portions 22. Accordingly, current can be applied stably.

The holder 3 is a portion that holds the pad 2. In the present embodiment, the holder 3 is made of hard resin and holds the attachment portion 2X of the pad 2 using double-sided adhesive tape. The holder 3 includes a pad holding portion 31 that holds the attachment portion 2X of the pad 2 on an upper surface 311, and wall portions 32 that are located at both ends of the pad holding portion 31. Note that the holding of the pad 2 is not limited to being achieved using double-sided adhesive tape and can be achieved using paste or an adhesive agent, for example.

The holder 3 is a non-conductor since it is made of hard resin. For this reason, if the pad 2 is arranged over the spine on the back of the user, the holder 3, which is a non-conductor, can be aligned with the spine, and the treatment portions 2Y of the pad 2 can be arranged so as to not overlap with the spine. Accordingly, it is possible to suppress a case in which a low-frequency pulse current flows in the spine and the spinal cord of the user. Accordingly, it is possible to suppress a case in which the spine and the spinal cord are injured by the current, and therefore the low-frequency treatment device 1 can be used safely. Also, since the portion of the attachment portion 2X of the pad 2 that overlaps with the spine does not need to be covered with a separate insulating member, the configuration of the combination of the pad 2 and the holder 3 can be simplified.

As shown in FIG. 2, the pad 2 is overlaid on the upper surface of the pad holding portion 31. Positioning protrusions 312 that are approximately U-shaped (approximately C-shaped) protrude on the pad holding portion 31, and the pad 2 can be positioned with respect to the holder 3 by aligning the edge portion of a window portion 23 that penetrates through the pad 2 in the top-underside direction with the positioning protrusions 312.

Since the pad 2 is a consumable product, it can be detached from the main body 4 at a time of replacement or the like. In the present embodiment, due to the holder 3 holding the pad 2, the holder 3 and the pad 2 are integrated, and the main body portion 4 is attached to and detached from the holder 3. The replacement of the pad 2 is performed together with the holder 3.

Figure 4A:
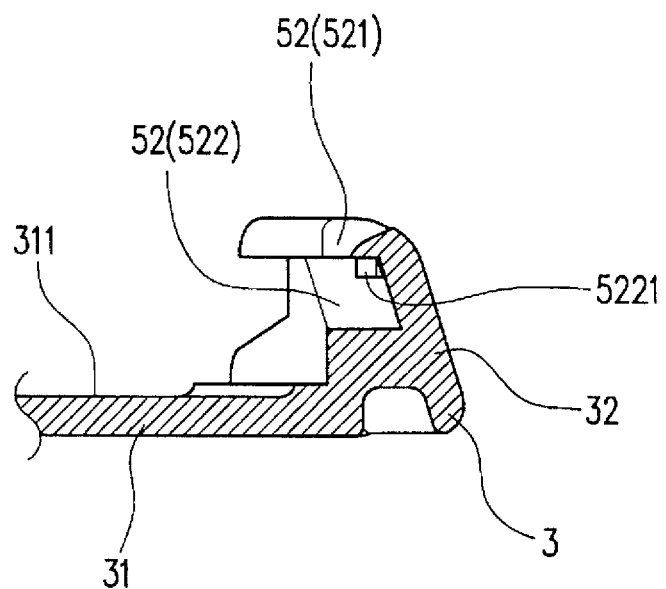
FIG. 4A is a vertical cross-sectional view showing relevant portions of an guiding engagement portion of the holder of the low-frequency treatment device.
Figure 4B:
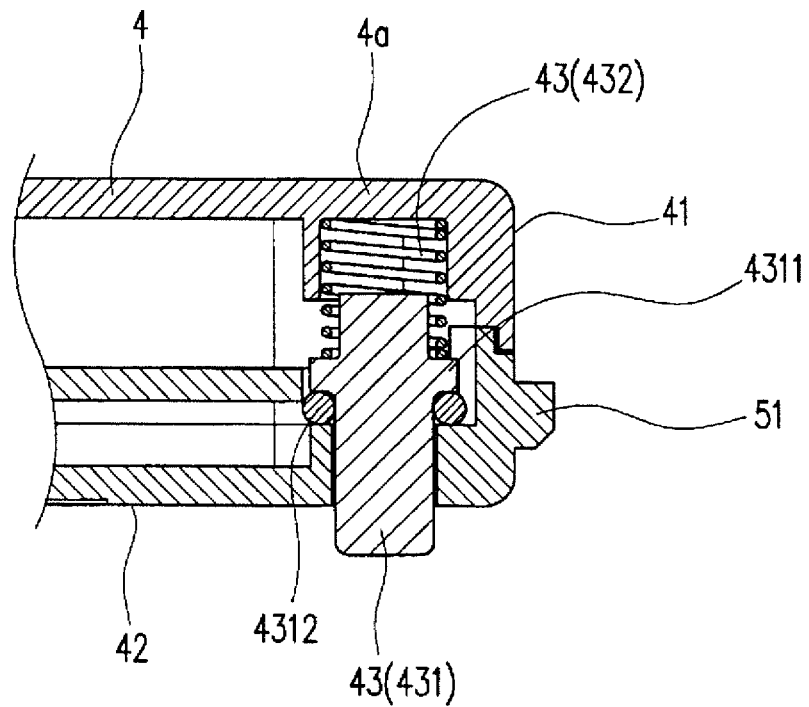
FIG. 4B is a vertical cross-sectional view showing relevant portions of the main body portion of the low-frequency treatment device.

The main body portion 4 is a portion that supplies a low-frequency pulse current to the conductive layers 2*a* of the pad 2 due to being attached to the holder 3. Inside of the main body portion 4, a power source unit such as a battery and an electrical circuit (substrate) for forming a desired low-frequency pulse current are arranged, and a switch and a display unit are provided outside of the main body portion 4 (only portions thereof are illustrated in the drawings). As shown in FIG. 4B, in a state of being biased by a downward biasing force P (see FIG. 6) generated by an electrode biasing portion 432, the main body portion-side electrode portion 43 protrudes from a lower surface 42, which is the surface of the case 4*a* of the main body portion 4 that directly opposes the holder 3. A main body portion-side electrode portion 43 is provided for each polarity.

Figure 6:
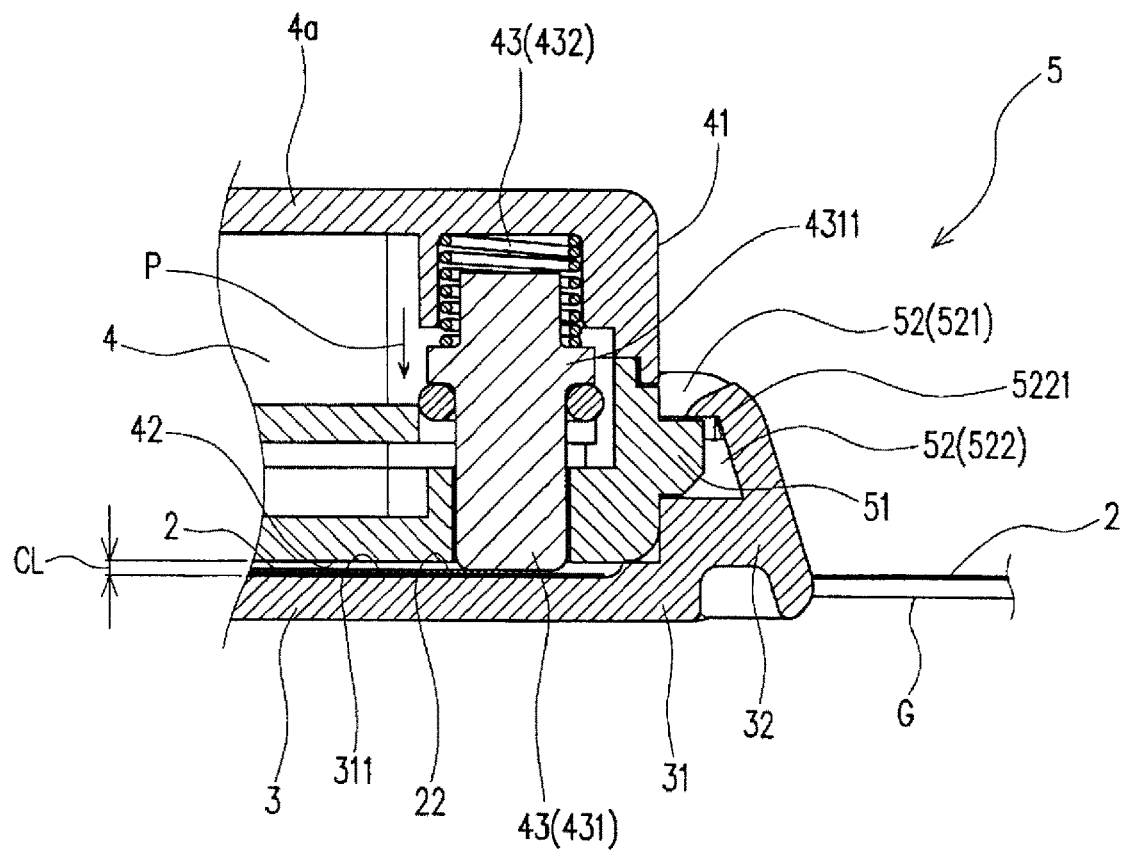
FIG. 6 is a vertical cross-sectional view showing relevant portions of an engaged state of the holder and the pad of the low-frequency treatment device.

At least a portion of the main body portion-side electrode portion 43 is composed of a conductor, and the main body portion-side electrode portion 43 includes an electrode body 431 that can protrude and recede with respect to the case of the main body portion, and the electrode biasing portion 432 that biases the electrode body 431 in the direction of protruding from the case. The electrode body 431 of the present embodiment has an approximately cylindrical shape that is formed entirely of metal. Also, the electrode body 431 includes a flange portion 4311 that protrudes in the radial direction, and downward protrusion of the electrode body from the case is restricted due to the flange portion 4311 abutting against the case (in the present invention, the flange portion 4311 abuts thereagainst through an O-ring 4312). The range above the restricted position is the range in which the main body portion-side electrode portion 43 can perform the movement. As shown in FIGS. 3 and 6, electrical conduction is established in the main body portion-side electrode portion 43 due to its leading end portion (more specifically, the leading end portion of the electrode body 431) coming into contact with the pad-side electrode portion 22.

In this manner, the electrode body 431 of the main body portion-side electrode portion 43 can be biased directly to the pad-side electrode portion 22 using the electrode biasing portion 432. Accordingly, the main body portion-side electrode portion 43 can be given a simple configuration. Also, since the pad-side electrode portion 22 is composed of a planar conductor as described above, as shown in FIG. 6, electrical conduction is established due to the planar pad-side electrode portion 22 coming into contact with the main body portion-side electrode portion 43 that is biased by the downward biasing force P generated by the electrode biasing portion 432. For this reason, stable electrical conduction is possible.

The main body portion-side electrode portion 43 of the present embodiment can perform movement in the direction of approaching and separating from the pad-side electrode portion 22 and is biased in the approaching direction. Also, as shown in FIG. 6, electrical conduction is established in the main body portion-side electrode portion 43 due to coming into contact with the pad-side electrode portion 22 in the range in which the movement is possible. With this configuration, the electrode body 431 of the main body portion-side electrode portion 43 is connected to the pad-side electrode portion 22 for electrical conduction while being biased by the biasing force P in the approaching direction in the range in which the movement is possible in the approaching and separating direction. For this reason, even if slack is generated in the engagement between the holder 3 and the main body portion 4, the main body portion-side electrode portion 43 biased by the biasing force P can follow the slack. In other words, since the electrical conduction is supported by the biasing, conduction failure can be suppressed.

Figure 8A:
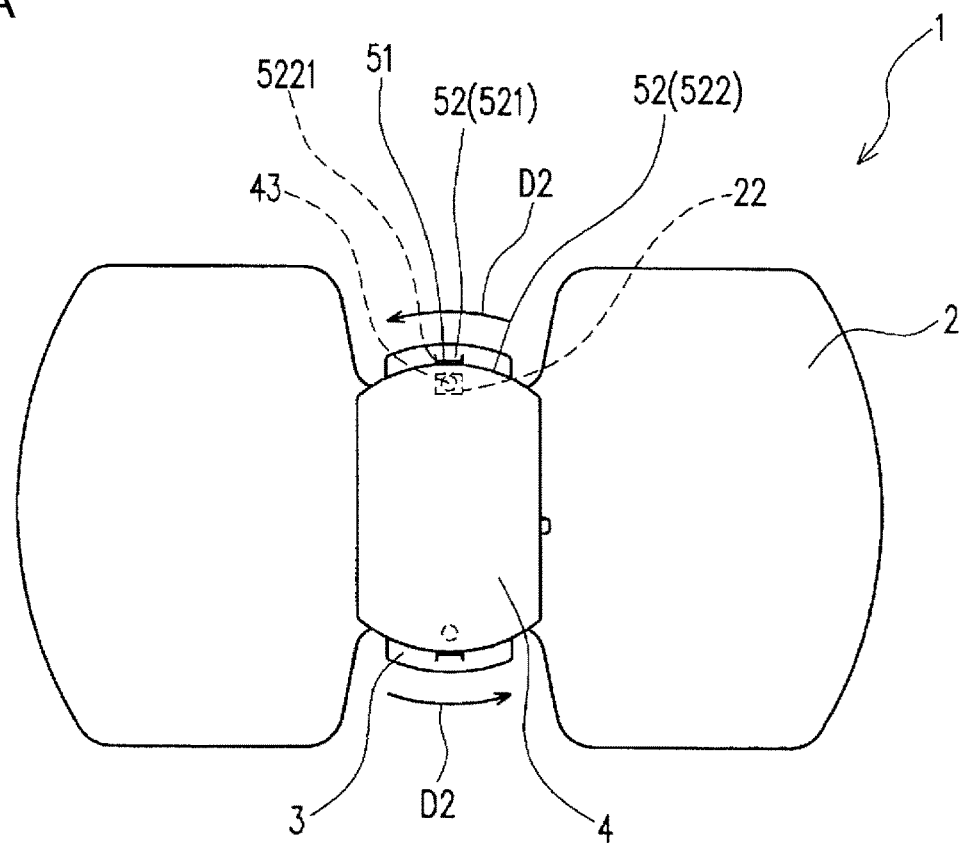
FIG. 8A is a plan view showing a state in which the main body portion is attached to the holder in the low-frequency treatment device.
Figure 8B:
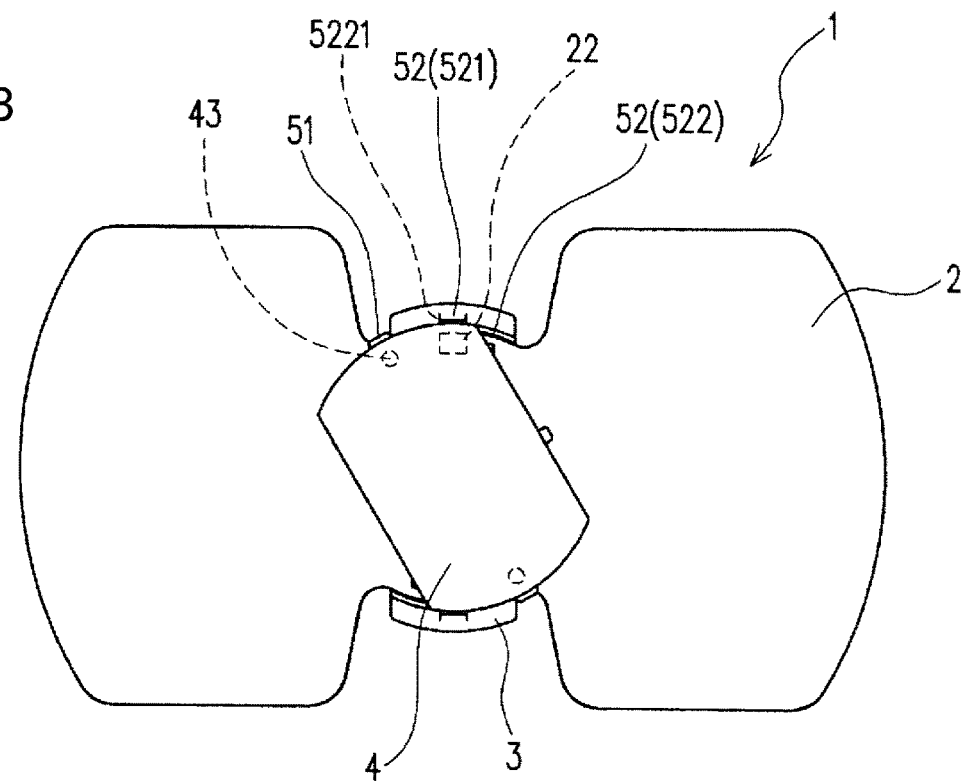
FIG. 8B is a plan view showing a state in which the main body portion is in the process of being removed from the holder in the low-frequency treatment device.

A guiding engagement portion 5 that is configured such that engagement occurs when the main body portion 4 is attached in an overlapping manner to the holder 3 and the engagement is canceled when the main body portion 4 is removed from the holder 3 is formed on the holder 3 and the main body portion 4. The guiding engagement portion 5 engages both the holder 3 and the main body portion 4 and restricts the movement direction of the main body portion 4 with respect to the holder 3 during attachment and removal of the two. Specifically, the guiding engagement portion 5 achieves engagement due to the holder 3 and the main body portion 4 moving in the opposing direction (downward direction) D1 indicated by the arrow in FIG. 2 during attachment of the holder 3 and the main body portion 4. Also, as shown in FIG. 8A, the guiding engagement portion 5 is formed such that the engagement between the holder 3 and the main body portion 4 is canceled as shown in FIG. 8B due to the main body portion 4 moving with respect to the holder 3 in the direction (horizontal direction) D2 that intersects the opposing direction D1 at the time of removing the holder 3 and the main body portion 4 as shown in FIG. 8A. Note that at the time of removal, movement in the direction (upward direction) opposite to the direction of movement at the time of attachment is not impossible. Also, in the present embodiment, in other words, the engagement between the holder 3 and the main body 4 is canceled if the main body portion 4 is moved in the clockwise direction, which is the direction opposite to the direction D2, which is the counterclockwise direction in plan view. Thus, it is possible to use a configuration in which engagement can be canceled by moving the main body portion 4 in both horizontal directions, and it is possible to use a configuration in which engagement can be canceled by moving the main body portion 4 in only one horizontal direction.

As shown in FIG. 2, the guiding engagement portion 5 of the present embodiment includes main body portion-side protrusions 51 that are protrusions formed on side surfaces 41 on the two sides in the lengthwise direction of the main body portion 4, and groove portions 52 that are formed on the holder 3 and into which the main body portion protrusions 51 fit. In this configuration, the guiding engagement portion 5 can be constituted by fitting together recesses and protrusions, and therefore the configuration can be simplified.

The wall portions 32 of the holder 3 are at both ends in the lengthwise direction of the pad holding portion 31, and are located on both sides (both end sides in the width direction of the pad 2) that sandwich the main body portion 4 in a direction intersecting the opposing direction D1. The inner sides of the wall portions 32 have curved shapes so as to allow rotation of the main body portion 4 during removal. As shown in FIG. 4A, a vertical groove portion 521 and a horizontal groove portion 522 are formed as the groove portion 52 on the inner surface of the wall portion 32. The vertical groove portion 521 is formed in the vertical direction, which is the direction D1 in which the holder 3 and the main body portion 4 oppose each other, and the upper portion of the vertical groove portion 521 is open. The horizontal groove portion 522 is formed in the horizontal direction that intersects (in the present embodiment, is orthogonal to) the vertical direction, and at least one end portion in the horizontal direction is open. In the present embodiment, the vertical groove portion 521 and the horizontal groove portion 522 are orthogonal to each other. Also, both ends in the horizontal direction of the horizontal groove portion 522 of the present embodiment are open.

Figure 5:
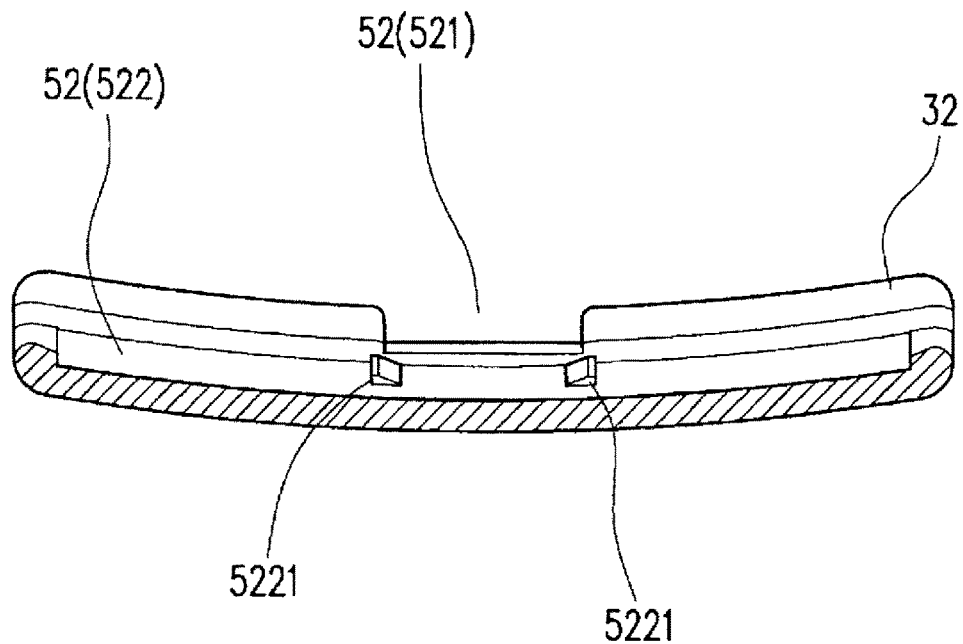
FIG. 5 is a horizontal cross-sectional perspective view showing the guiding engagement portion of the holder of the low-frequency treatment device.

Also, as shown in FIG. 8A, the horizontal groove portions 522 are provided with stopper protrusions 5221 and 5221 serving as rotation restricting portions that restrict rotation of the main body portion 4 in the horizontal direction D2, for example, with respect to the holder 3 from the state in which the main body portion 4 is attached so as to overlap with the holder 3. As shown in FIG. 5, the stopper protrusions 5221 and 5221 are located on both sides in the lateral direction, which sandwich the main body portion-side protrusions 51. When an attempt is made to move the main body portion-side protrusions 51, the main body portion-side protrusions 51 abut against the stopper protrusions 5221. Due to this abutting, movement in the direction of canceling the engagement of the main body portion 4 is restricted. In the present embodiment, since the engagement can be canceled by moving the main body portion 4 in both horizontal directions, the stopper protrusions 5221 are formed at two locations. However, in the case of using a configuration in which the engagement is canceled by moving the main body portion 4 in only one horizontal direction, a stopper protrusion 5221 need only be formed at one location.

As shown in FIG. 6, the holder 3 (upper surface 311) and the main body portion 4 (lower surface 42) include a clearance CL of a predetermined distance in the attached state. The clearance CL has a distance in the vertical direction according to which the pad 2 can be arranged between the holder 3 (upper surface 311) and the main body portion 4 (lower surface 42). The electrical conduction is established due to the pad-side electrode portion 22 and the main body portion-side electrode portion 43 coming into contact with each other in the clearance CL of the predetermined distance.

The main body portion 4 can be removed from the holder 3 by being rotated in plan view with respect to the holder 3 so as to reach the state shown in FIG. 8B from the state shown in FIG. 8A. As described above, the holder 3 includes the stopper protrusions 5221 and 5221.

Figure 7:
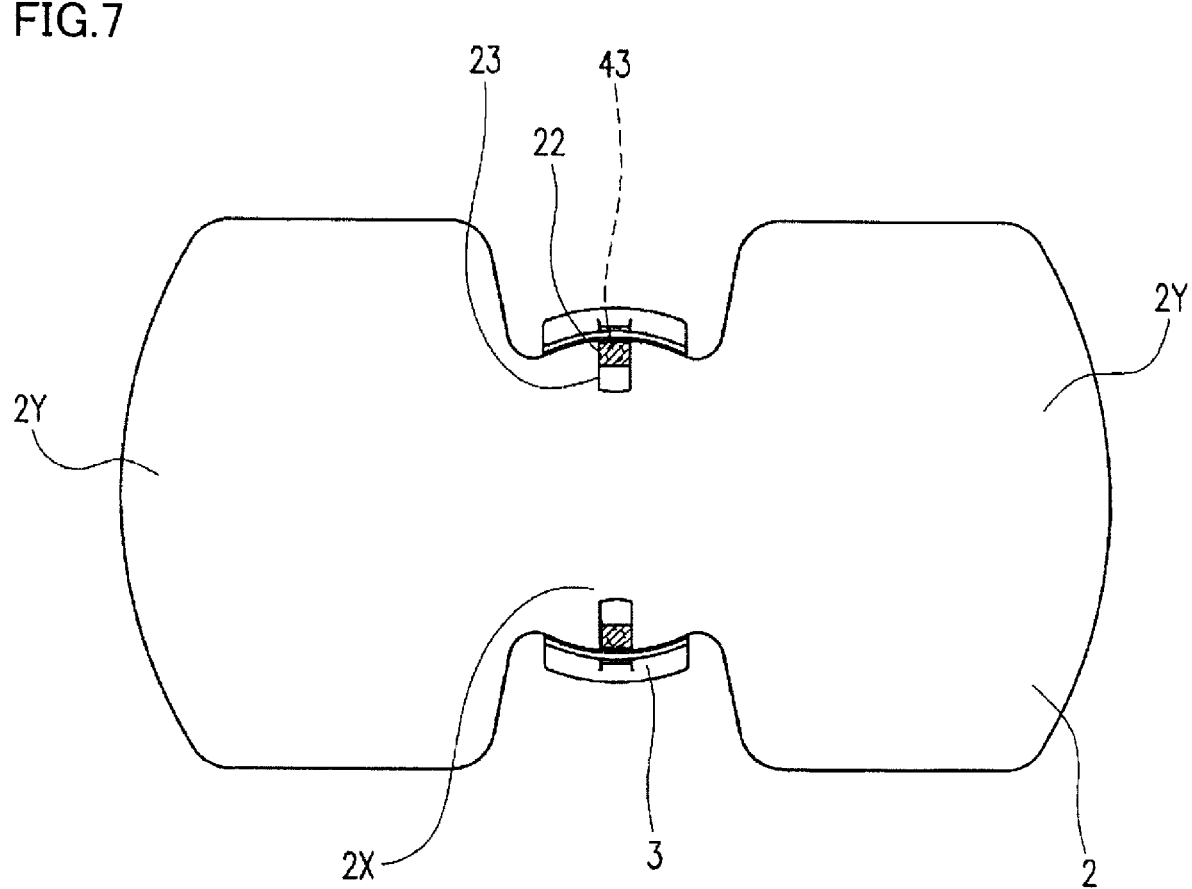
FIG. 7 is a plan view showing the holder and the pad of the low-frequency treatment device, a pad-side electrode portion being formed with a smaller area than that shown in FIG. 3.

In particular, if, as shown in FIG. 7, the pad-side electrode portion 22 is formed with an area that is smaller in comparison to that shown in FIG. 3, in the case where the main body portion 4 is at a position at which rotation is restricted by the stopper protrusion 5221 as shown in FIG. 8A, electrical conduction is established between the pad-side electrode portions 22 and the main body portion-side electrode portions 43, and in the case where the main body portion 4 is not at a position at which rotation is restricted as shown in FIG. 8B for example, the electrical conduction can be prevented from being established due to the pad-side electrode portions 22 (only one side is illustrated with a broken line) and the main body portion-side electrode portions 43 being separated from each other. If the pad-side electrode portion 22 is formed into the shape shown in FIG. 7, electrical conduction is achieved only when the holder 3 and the main body portion 4 are in the attached state, and therefore if the main body portion 4 has not been attached correctly, current will not be applied to the pad 2, which is safe.

In this manner, the dimensions of the pad-side electrode portions 22 can be set so as to correspond to the range in which the main body portion-side electrode portions 43 can perform the movement in the state in which the main body portion 4 is engaged with the holder 3. In other words, in the engaged state, the pad-side electrode portions 22 can be set to have dimensions that approximately match the range in which the main body-side electrode portions 43 can perform the movement, which is determined by the stopper protrusions 5221 and 5221 and corresponds to the range of play of the main body portion 4 with respect to the holder 3. Accordingly, the electrical conduction between the pad-side electrode portions 22 and the main body portion-side electrode portions 43 will be canceled if not in the engaged state as described above, and therefore if the main body portion 4 has not been correctly attached to the holder 3 or the main body portion 4 is misaligned from the holder 3, treatment cannot be performed, which is safe. Also, the user can be prompted to correctly attach the main body portion 4.

Although an embodiment of the present invention has been described above, the present invention is not limited to the above-described embodiment, and various modifications can be added thereto without departing from the gist of the present invention.

For example, pads 2 may be formed separately for each polarity. Also, in the above-described embodiment, the exposed portions of the conductive layers 2a that are formed for the electrical connection with the main body portion-side electrode portions 43 are located on both sides in the width direction of the attachment portion 2X, but there is no limitation to this, and another position such as the center in the width direction may be used, as long as it overlaps with the main body portion 4 when attached. Also, conversely to the above-described embodiment, protrusions may be formed on the holder 3 and groove portions may be formed on the main body portion 4.

Figure 9:
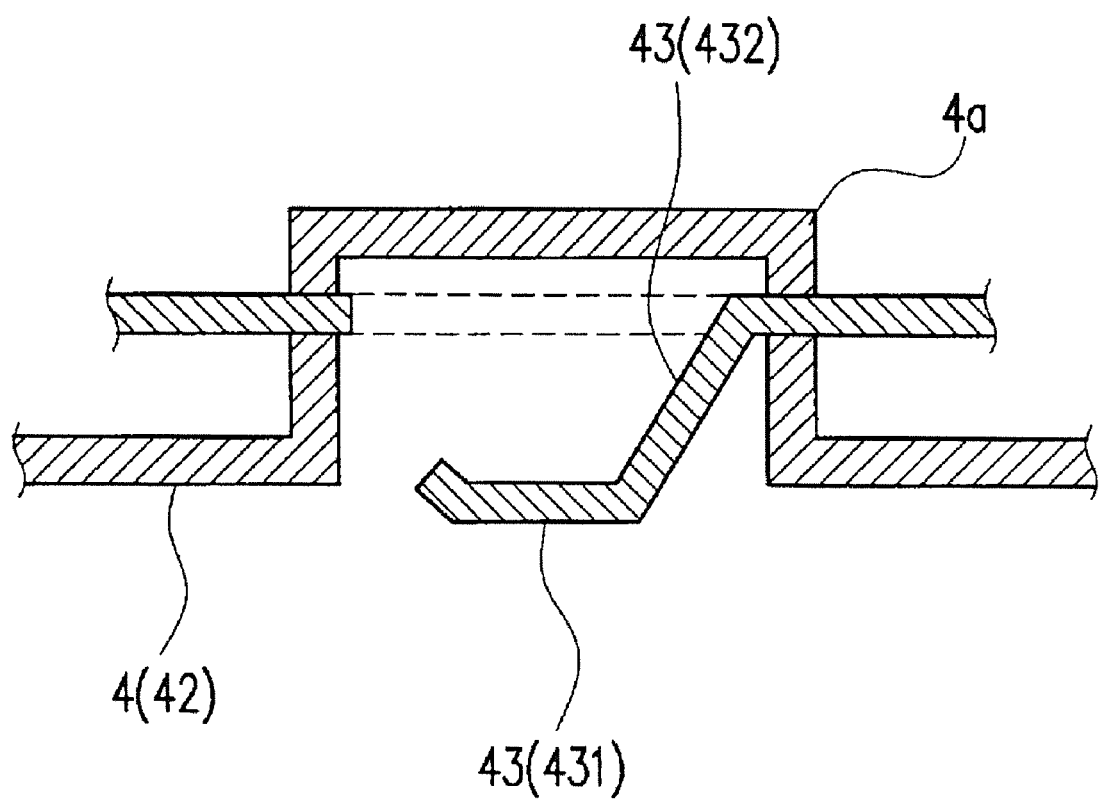
FIG. 9 is a vertical cross-sectional view schematically showing relevant portions of a main body portion-side electrode portion in a low-frequency treatment device according to another embodiment of the present invention.

Also, the main body portion-side electrode portions 43 can have electrode bodies 431 and electrode biasing portions 432 that are formed integrally with each other. For example, in the embodiment shown in FIG. 9, a main body portion-side electrode portion 43 is formed into a plate spring shape, the leading end side thereof being the electrode body 431, and the base end side thereof being the electrode biasing portion 432. The electrode biasing portion 432 is fixed to the case 4a of the main body portion 4. In this embodiment, the electrode body 431 can be caused to protrude downward from the lower surface 42 of the main body portion 4 mainly due to the biasing force generated by the electrode biasing portion 432. Also, the main body portion-side electrode portion 43 can be formed into various shapes other than a plate spring shape (e.g., a coil spring shape, etc.).

Also, the main body portion-side electrode portions 43 of the present embodiment can perform movement in the direction of approaching and separating from the pad-side electrode portions 22 and are biased in the approaching direction. However, there is no limitation to this, and it is also possible to use a configuration in which the pad-side electrode portions 22 can perform movement in the direction of approaching and separating from the main body portion-side electrode portions 43 and are biased in the approaching direction. This kind of configuration is realized by, for example, forming biasing portions that generate a biasing force toward the main body portion 4 on the holder 3 and applying the biasing force of the holder 3 to the pad 2 attached to the holder 3.

Figure 10:
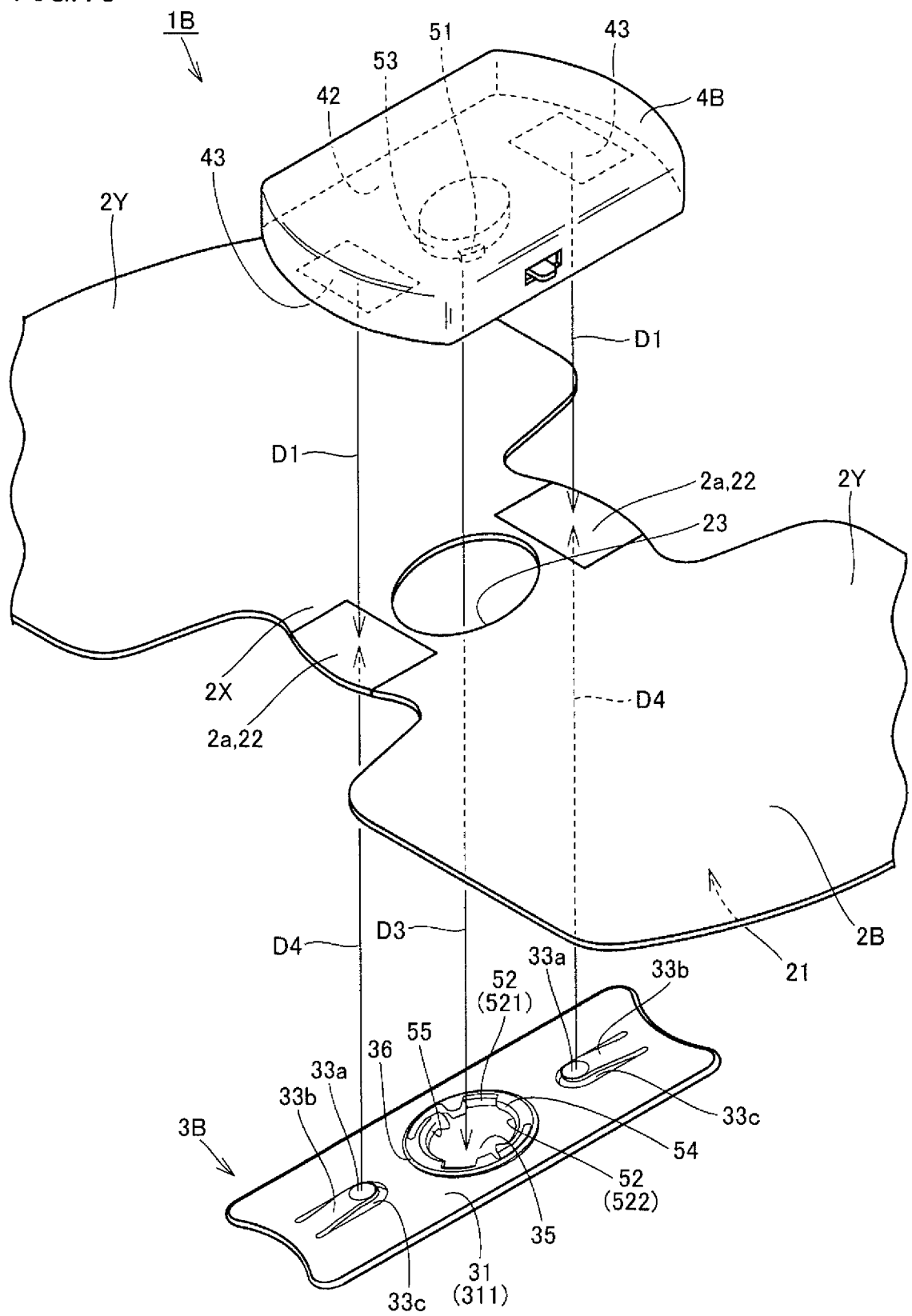
FIG. 10 is an exploded perspective view showing a state in which a holder, a pad, and a main body portion are separated from each other in a low-frequency treatment device according to yet another embodiment of the present invention.

Hereinafter, a configuration in which the pad-side electrode portions 22 can perform movement in the direction of approaching and separating from the main body portion-side electrode portions 43 and are biased in the approaching direction will be described as yet another configuration of an embodiment with reference to FIGS. 10 to 12. In other words, a low-frequency treatment device 1B shown in FIG. 10 includes a pad 2B, a holder 3B, and a main body portion 4B.

The low-frequency treatment device 1B shown in FIG. 10 and the low-frequency treatment device 1 according to the above-described embodiment differ in the following respects. Note that parts of the configuration of the low-frequency treatment device 1B that are the same as or correspond to those of the low-frequency treatment device 1 are denoted by identical reference numerals and redundant description thereof is not repeated.

The main body portion 4B included in the low-frequency treatment device 1B includes a lower surface 42, which is a surface that directly opposes the holder 3B, and the surface of the lower surface 42 is provided with a pair of main body portion-side electrode portions 43. The main body portion-side electrode portions 43 each have a flat plane shape, unlike in the case of the above-described embodiment. The main body portion-side electrode portions 43 cannot perform movement in the direction of approaching and separating from pad-side electrode portions 22 and are not biased in the approaching direction. A cylindrical insertion portion 53 is provided in the center of the lower surface 42 of the main body portion 4B so as to hang down from the lower surface 42. Main body portion-side protrusions 51 are provided so as to protrude on the outer circumferential surface of the insertion portion 53.

The pad 2B included in the low-frequency treatment device 1B is provided with a circular window portion 23 that penetrates through the pad 2B in the top-underside direction. The window portion 23 has a size that allows insertion of the insertion portion 53 and the main body portion-side protrusions 51 provided on the main body portion 4B. When the main body portion 4B is attached to the pad 2B and the holder 3B, the insertion portion 53 and the main body portion-side protrusions 51 are inserted into a through hole 35 (described later) of the holder 3B through the window portion 23 (arrow D3).

The holder 3B included in the low-frequency treatment device 1B includes a pad holding portion 31. The holder 3B does not include a wall portion 32 (see FIG. 2), unlike in the case of the above-described holder 3 (see FIG. 2). The pad holding portion 31 has an approximate plate shape overall, and can hold the attachment portion 2X of the pad 2B on the upper surface 311 of the pad holding portion 31. The through hole 35 is provided in the center of the pad holding portion 31.

Figure 11:
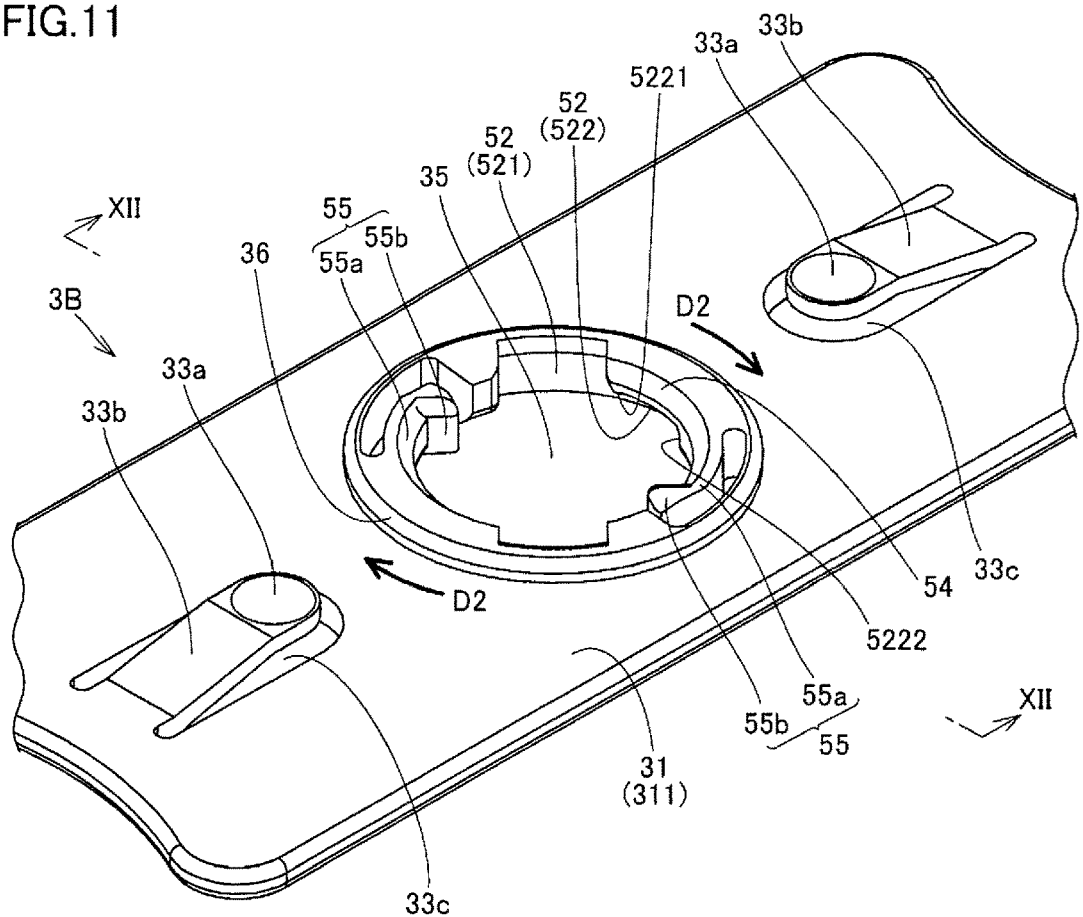
FIG. 11 is a perspective view showing the holder (viewed from above) included in the low-frequency treatment device according to yet another embodiment of the present invention.
Figure 12:
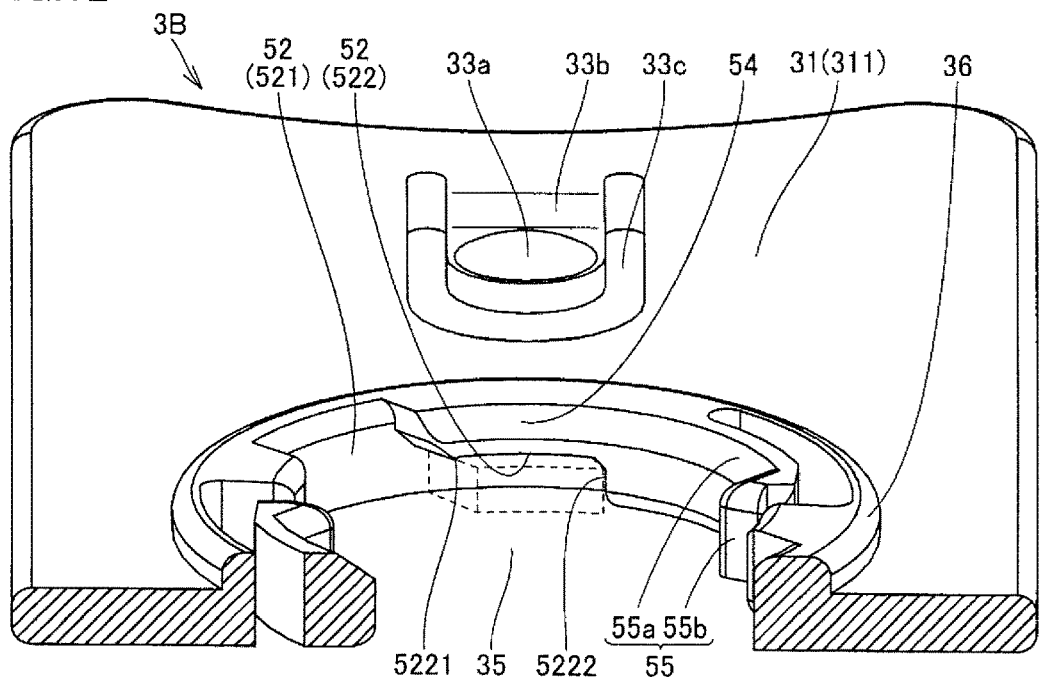
FIG. 12 is a cross-sectional view taken along line XII-XII in FIG. 11 and viewed in the direction of arrows.

On the upper surface 311 of the pad holding portion 31, a portion 36 located in the periphery of the through hole 35 protrudes in the form of a ring from the upper surface 311 (see FIG. 11 as well). Positioning of the pad 2B with respect to the holder 3B can be performed by matching the inner circumferential edge portion of the window portion 23 of the pad 2B with the portion 36 that protrudes in the form of a ring.

FIG. 11 is a perspective view showing the holder 3B (a view from the upper surface side thereof). FIG. 12 is a cross-sectional view taken along line XII-XII in FIG. 11 and viewed in the direction of arrows. As shown in FIGS. 11 and 12, groove portions 52 into which the main body portion-side protrusions 51 (FIG. 10) are to be fit are provided on the inner side of the through hole 35 of the holder 3B. The groove portions 52 each include a vertical groove portion 521 and a horizontal groove portion 522. The vertical groove portion 521 is formed in the vertical direction, which is the direction D1 (FIG. 10) in which the holder 3B and the main body portion 4B oppose each other. The horizontal groove portion 522 is formed in the horizontal direction that intersects (here, is orthogonal to) the vertical direction, and at least one end portion in which horizontal direction is open. A brim portion 54 that protrudes inward in the radial direction is provided in the upper portion of the horizontal groove portion 522.

A stopper protrusion 5221 and a wall portion 5222 are formed in the horizontal groove portion 522. The stopper protrusion 5221 is located on the side on which the opening of the vertical groove portion 522 is formed, and the wall portion 5222 is located on the side opposite thereto. The stopper protrusion 5221 and the wall portion 5222 function as rotation restricting portions.

The insertion portion 53 (FIG. 10) of the main body portion 4B is inserted into the through hole 35 of the holder 3B and the main body portion 4B is rotated with respect to the holder 3B in the direction of the arrows D2 (see FIG. 11). Accordingly, the main body portion-side protrusions 51 (FIG. 10) are arranged between the stopper protrusions 5221 and the wall portions 5222 (below the brim portions 54), and the main body portion 4B is attached to the holder 3B.

If an attempt is made to move the main body portion-side portions 51 in the rotation direction, the main body portion-side protrusions 51 abut against the stopper protrusions 5221 and the wall portions 5222. Due to this abutting, movement in the direction of canceling the engagement of the main body portion 4B is restricted. Also, due to the main body portion-side protrusions 51 engaging with the brim portions 54 provided above the horizontal groove portions 522, movement in which the main body portion 4B separates from the holder 3B is restricted. In this state, the stopper protrusions 5221 and the wall portions 5222 restrict rotation of the main body portion 4B with respect to the holder 3B in the direction opposite to that of the arrows D2.

Furthermore, a pair of holding pieces 55 that have cantilever shapes and extend in the circumferential direction are provided on the inner side of the through hole 35. The holding pieces 55 each include a plate spring portion 55a that extends in the circumferential direction, and a protrusion portion 55b that is provided on the leading end of the plate spring portion 55a and has a shape that protrudes toward the inner side in the radial direction. When the insertion portion 53 (FIG. 10) of the main body portion 4B is inserted into the through hole 35 of the holder 3B, the pair of holding pieces 55 sandwich the insertion portion 53 of the main body portion 4B, whereby it is possible to make it difficult for the main body portion 4B to rotate with respect to the holder 3B, and by extension, to make it more difficult for the main body portion 4B to come off of the holder 3B.

Also, the holder 3B is provided with a pressing portion 33a and a biasing portion 33b. The pressing portion 33a and the biasing portion 33b are provided with a cut-out 33c in their periphery, and thus are formed into a plate spring shape overall. The leading end side is the pressing portion 33a and the base end side is the biasing portion 33b. The biasing portion 33b is fixed to the pad holding portion 31 of the holder 3B.

The pressing portion 33a is arranged on the side opposite to the side on which the main body portion-side electrode portion 43 is arranged with respect to the pad-side electrode portion 22. The pressing portion 33a is arranged so as to come into contact with the underside surface of the pad-side electrode portion 22, and can protrude and recede with respect to the pad-side electrode portion 22. The biasing portion 33b biases the pressing portion 33a upward in the protrusion direction from the upper surface 311 of the pad holding portion 31. In other words, in the state in which the main body portion 3B, the pad 2B, and the holder 3B are attached to each other (see arrows D1 and D4 in FIG. 10), the pad-side electrode portion 22 can perform movement in the direction of approaching and separating from the main body portion-side electrode portion 43 (FIG. 10) and is biased in the approaching direction by the pressing portion 33a and the biasing portion 33b.

According to this configuration, even if slack is generated in the engagement between the holder 3B and the main body 4B, the biased pad-side electrode portion 22 can follow the slack. That is, the electrical conduction between the pad-side electrode portion 22 and the main body portion-side electrode portion 43 is supported by biasing, and therefore conduction failure can be suppressed. In this configuration, the main body portion-side electrode portion 43 need not perform movement in the direction of approaching and separating from the pad-side electrode portion 22 and need not be biased in the approaching direction. With this configuration as well, the pad-side electrode portion 22 can perform movement in the direction of approaching and separating from the main body portion-side 43 and is biased in the approaching direction, whereby the electrical conduction is supported by the biasing of the pad-side electrode portion 22. For this reason, conduction failure can be suppressed. Alternatively, in the above-described configuration, the main body portion-side electrode portion 43 may perform movement in the direction of approaching and separating from the pad-side electrode portion 22 and may be biased in the approaching direction. The electrical conduction is supported by the biasing of the main body portion-side electrode portion 43 and by the biasing of the pad-side electrode portion 22, and therefore conduction failure is further suppressed.

Although embodiments have been described above, the content disclosed above is in all respects exemplary and in no respects limiting. The technical scope of the present invention is indicated by the claims, and all meanings and modifications within the scope that are equivalent to the claims are intended to be encompassed therein.

REFERENCE SIGNS LIST 1, 1B Low-frequency treatment device
2, 2B Pad
2X Attachment portion
2Y Treatment portion
2a Conductive layer
3, 3B Holder
4, 4B Main body portion
4a Case
5 Guiding engagement portion
21 Body-side portion
22 Pad-side electrode portion
23 Window portion
31 Pad holding portion
32 Wall portion
33a Pressing portion
33b Biasing portion
35 Through hole
36 Portion
41 Side surface
42 Lower surface
43 Main body portion-side electrode portion
51 Main body portion-side protrusion
52 Groove portion
53 Insertion portion
54 Brim portion
55 Holding piece
55a Plate spring portion
55b Projection portion
311 Upper surface
312 Positioning protrusion
431 Electrode body
432 Electrode biasing portion
521 Vertical groove portion
522 Horizontal groove portion
4311 Flange portion
4312 O ring
5221 Stopper protrusion (rotation restricting portion)
5222 Wall portion (rotation restricting portion)
CL Clearance

The invention claimed is:
1. A low-frequency treatment device comprising:
a pad configured to be attached to a body of a user and to supply a low-frequency pulse current to the user, the pad including a pad-side electrode portion;
a holder configured to hold the pad; and
a main body portion configured to be attached to the holder, the main body portion including a main body portion-side electrode portion configured to be connected to the pad-side electrode portion for electrical conduction and to supply a low-frequency pulse current thereto,
wherein the holder and the main body portion are engaged with a clearance of a predetermined distance therebetween for arranging the pad,
the electrical conduction is established between the pad-side electrode portion and the main body portion-side electrode portion due to coming into contact with each other in the clearance so that the pad-side electrode portion and the main body portion-side electrode portion directly contact each other,
one electrode portion among the pad-side electrode portion and the main body portion-side electrode portion can perform movement in a direction of approaching and separating from the other electrode portion and is biased in an approaching direction,
the electrical conduction is established in the one electrode portion in a range in which the movement is possible, and
the holder includes:
a pad holding portion configured to hold the pad on its upper surface;
a pressing portion that is arranged on the pad-side electrode portion on a side opposite the main body portion-side electrode portion, the pressing portion being able to protrude and recede with respect to the pad holding portion; and
a biasing portion that biases the pressing portion in a direction of protruding from the pad holding portion.

2. The low-frequency treatment device according to claim 1, wherein the holder is composed of a non-conductor.

3. A main body portion for a low-frequency treatment device including: a pad configured to be attached to a body of a user and to supply a low-frequency pulse current to the user, the pad including a pad-side electrode portion; and a holder configured to hold the pad, the main body portion being configured to be attached to a holder and comprising:
a main body portion-side electrode portion configured to be connected to a pad-side electrode portion for electrical conduction and to supply a low-frequency pulse current thereto,
wherein the main body portion is configured to engage with the holder, with a clearance of a predetermined distance therebetween for arranging the pad,
the electrical conduction is established due to the main body portion-side electrode portion coming into contact with the pad-side electrode portion in the clearance so that the pad-side electrode portion and the main body portion-side electrode portion directly contact each other, and
the main body portion-side electrode portion can perform movement in a direction of approaching and separating from the pad-side electrode portion and is biased in an approaching direction,
the electrical conduction is established in a range in which the movement is possible, and
the holder includes:
a pad holding portion configured to hold the pad on its upper surface;
a pressing portion that is arranged on the pad-side electrode portion on a side opposite the main body portion-side electrode portion, the pressing portion being able to protrude and recede with respect to the pad holding portion; and
a biasing portion that biases the pressing portion in a direction of protruding from the pad holding portion.

4. A pad for a low-frequency treatment device, configured to be attached to a body of a user and to supply a low-frequency pulse current to the user, the pad comprising:

a pad-side electrode portion, wherein the pad is configured to be held by a holder, a main body portion is attached to the holder, the main body portion includes a main body portion-side electrode portion configured to be connected to the pad-side electrode portion for electrical conduction and to supply a low-frequency pulse current thereto, the holder and the main body portion are engaged with a clearance of a predetermined distance therebetween for arranging the pad, the electrical conduction is established between the pad-side electrode portion and the main body portion-side electrode portion due to coming into contact with each other in the clearance so that the pad-side electrode portion and the main body portion-side electrode portion directly contact each other, one electrode portion among the pad-side electrode portion and the main body portion-side electrode portion can perform movement in a direction of approaching and separating from the other electrode portion and is biased in an approaching direction, the electrical conduction in the one electrode portion is established in a range in which the movement is possible, the electrical conduction in the main body portion-side electrode portion is established due to its leading end portion coming into contact with the pad-side electrode portion, the pad-side electrode portion is composed of a planar conductor, and the holder includes:

a pad holding portion configured to hold the pad on its upper surface;

a pressing portion that is arranged on the pad-side electrode portion on a side opposite the main body portion-side electrode portion, the pressing portion being able to protrude and recede with respect to the pad holding portion; and a biasing portion that biases the pressing portion in a direction of protruding from the pad holding portion.

5. The combination of a pad and a holder for a low-frequency treatment device according to claim 4, wherein the holder is composed of a non-conductor.

6. A combination of a pad and a holder for a low-frequency treatment device, comprising:

a pad configured to be attached to a body of a user and to supply a low-frequency pulse current to the user, the pad including a pad-side electrode portion; and a holder that holds the pad, wherein the holder is configured to attach to a main body portion, and the main body portion includes a main body portion-side electrode portion configured to be connected to the pad-side electrode portion for electrical conduction and to supply a low-frequency pulse current thereto, the holder and the main body portion are configured to engage with a clearance of a predetermined distance therebetween for arranging the pad, the electrical conduction is established between the pad-side electrode portion and the main body portion-side electrode portion due to coming into contact with each other in the clearance so that the pad-side electrode portion and the main body portion-side electrode portion directly contact each other, one electrode portion among the pad-side electrode portion and the main body portion-side electrode portion can perform movement in a direction of approaching and separating from the other electrode portion and is biased in an approaching direction, the electrical conduction in the one electrode portion is established in a range in which the movement is possible, the main body portion can be removed from the holder by being rotated in plan view with respect to the holder, the holder includes a rotation restricting portion that restricts rotation of the main body portion in the attached state, the pad-side electrode portion is formed such that if the main body portion is at a position at which rotation is restricted by the rotation restricting portion, the electrical conduction is established, and if the main body portion is not at a position at which rotation is restricted, the electrical conduction is not established due to the pad-side electrode portion and the main body portion-side electrode portion being separated from each other, and the holder includes:

a pad holding portion configured to hold the pad on its upper surface;

a pressing portion that is arranged on the pad-side electrode portion on a side opposite the main body portion-side electrode portion, the pressing portion being able to protrude and recede with respect to the pad holding portion; and a biasing portion that biases the pressing portion in a direction of protruding from the pad holding portion.

* * * * *